(12) United States Patent
Follstad et al.

(10) Patent No.: US 7,384,765 B1
(45) Date of Patent: *Jun. 10, 2008

(54) CELL CULTURE PERFORMANCE WITH BETAINE

(75) Inventors: Brian D. Follstad, Seattle, WA (US); Anne H. Potter, Sammamish, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/437,418

(22) Filed: May 19, 2006

Related U.S. Application Data

(62) Division of application No. 10/226,931, filed on Aug. 23, 2002, now Pat. No. 7,067,279.

(51) Int. Cl.
*C12P 21/06* (2006.01)

(52) U.S. Cl. ...................................... 435/69.1

(58) Field of Classification Search ............ None
See application file for complete search history.

(56) References Cited

U.S. PATENT DOCUMENTS

| | | | |
|---|---|---|---|
| 5,122,469 A | 6/1992 | Mather et al. | |
| 5,633,162 A | 5/1997 | Keen et al. | |
| 5,705,364 A | 1/1998 | Etcheverry et al. | |

OTHER PUBLICATIONS

Kim et al., "Osmoprotective Effect of Glycine Betaine on Thrombopoietin Production in Hyperosmotic Chinese Hamster Ovary Cell Culture Clonal Variations," Biotechnol Prog 16:775-781 (2000).
Petronini et al., "Modulation by Betaine of Cellular Responses to Osmotic Stress," Biochem J. 15;282 (Pt 1) 69-73 (1992).
Rasmussen et al., "Isolation, characterixation and recombinant protein expression in Veggie-CHO: A serum-free CHO host cell line," Cytotechnology, 28:31-42 (1998).
Ryu et al., "Osmoprotective Effect of Glycine Betaine on Foreign Protein Production in Hyperosmotic Recombinant Chinese Hamster Ovary Cell Cultures Differs Among Cell Lines," Biotech Bioeng., 70:167-175 (2000).
Urlaub et al., "Isolation of Chinese hamster cell mutants deficient in dihydrofolate reductase activity" Proc. Natl. Acad Sci USA 77:4216-4220 (1980).

*Primary Examiner*—Robert B. Mondesi
(74) *Attorney, Agent, or Firm*—Marshall, Gerstein & Borun LLP

(57) ABSTRACT

This invention relates generally to the field of cell culture. More particularly, the invention relates to improving viability of recombinant cell cultures and the yields of secreted polypeptides therefrom by the addition of betaine to the tissue culture medium.

14 Claims, 1 Drawing Sheet

CELL CULTURE PERFORMANCE WITH BETAINE

This application is a divisional of U.S. patent application Ser. No. 10/226,931 filed Aug. 23, 2002, now U.S. Pat. No. 7,067,279.

FIELD OF THE INVENTION

This invention relates generally to the field of cell culture. More particularly, the invention relates to improving viability of recombinant cells in culture and the yields of secreted polypeptides therefrom by the addition of betaine to the tissue culture medium.

BACKGROUND

Many commercially important polypeptides are recombinantly produced in cells that are adapted grown in culture. One of the limits to growing cell lines in culture is the decreased viability of the cells over time, which is partially rectified by the addition of growth factors. However, while this extra step improves cell viability, it adds significant costs to the production of the desired recombinant polypeptide.

Betaine has been shown to counteract the effects of hyperosmotic conditions in cell cultures in vitro, and also counteracts the denaturing tendency of urea (Kim et al., (2000) Biotechnol. Prog., 16:775-781; Ryu et al., (2000) Biotech. Bioeng., 70:167-175). However, it was also reported that betaine had no effect on cell culture growth or maximum viable cell concentration when cultures were at physiological ranges, i.e., 292 mOsm/kg, of osmolality (Ryu et al., (2000) Biotech. Bioeng., 70:167-175).

Thus, there is a need in the art for methods of improving the cell viability of cell cultures so as to reduce cell death, to reduce the dependence on growth factors to increase recombinant polypeptide production while not increasing costs. The invention fulfills this need by providing a simple, easy and inexpensive way of increasing cell viability and reducing the requirement for growth factors by cultured cells.

SUMMARY OF THE INVENTION

In the invention provided herein, betaine is added to medium used for culturing cells producing recombinant polypeptides in vitro. Cell cultures grown in such medium demonstrated improved cell viability and recombinant polypeptide production.

Accordingly in one aspect, the invention provides a method comprising culturing cells recombinantly engineered to express a protein of interest in tissue culture medium wherein the medium has an effective amount of betaine wherein the tissue culture medium is not hyperosmotic, and whereby cell survival is improved relative to cells grown without betaine.

In a particular aspect, the invention provides a method comprising culturing animal cells recombinantly engineered to express a protein of interest in tissue culture medium wherein the medium has an effective amount of betaine wherein the tissue culture medium is not hyperosmotic, and whereby the animal cell survival is improved relative to cells grown without betaine.

Mammalian cells are advantageously used in the method of the invention, and particularly CHO cells. The betaine can be, for example, betaine or any derivative thereof. The invention finds particular use in the culturing of animal cells that are genetically engineered to secrete a polypeptide of interest.

DETAILED DESCRIPTION OF THE INVENTION

Figure 1:
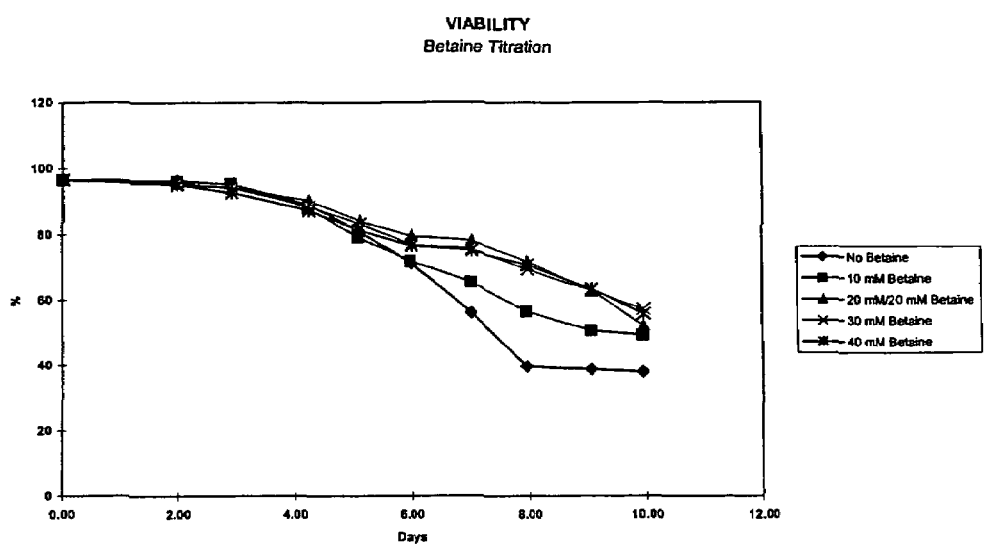
FIG. 1. Addition of betaine to a recombinant cell culture (expressing huTNFR-Fc) increases cell viability. The viable cells are shown as a percentage of living cells over total cells when measured by trypan blue exclusion staining during the course of the culture.

The invention is based, in part, on the discovery that betaine can be used to improve the performance and growth of cell cultures. Specifically, betaine acts to increase cell viability in essentially serum free media and thus increases recombinant polypeptide production of cell cultures, thereby enhancing culture robustness, and also reduces the reliance on the addition of growth factors to the medium, thereby reducing costs associated with recombinant polypeptide production.

In illustrative, non-limiting examples described below, betaine was used as a model compound to increase cell viability and increase polypeptide production in a serum free recombinant mammalian cell culture system where osmolality was near physiological conditions. In particular, it is shown that addition of betaine to the medium increases cell viability and production of recombinant polypeptides. These results demonstrate that betaine can be used to improve the performance of in vitro animal cell culture systems.

While the working examples provide a description of animal cells grown in the presence of betaine in non-hyperosmotic conditions that demonstrate improved viability concomitant with improved production of recombinant polypeptides, it will be understood by one of skill in the art that non-animal cells such as prokaryotic cells, e.g., E. coli, insect cells, e.g., Sf9, plant cells, yeast cells or the like can also be grown in the presence of betaine in normal osmotic conditions such that viability is improved and recombinant production of polypeptides is enhanced. However, the invention is particularly advantageous for growing industrially important animal cell lines that have been adapted to grow in long-term culture and are producing recombinant polypeptides of interest.

By animal cell is meant a cell whose progenitors were derived from a multicellular animal. Preferably, the animal cell lines are mammalian cell lines. A wide variety of animal cell lines suitable for growth in culture are available from, for example, the American Type Culture Collection (ATCC, Manassas, Va.) and NRRL (Peoria, Ill.). Some of the more established cell lines typically used in the industrial or academic laboratory and which are preferred are CHO, VERO, BHK, HeLa, Cos, CV1, MDCK, 293, 3T3, PC12, hybridoma, myeloma, and WI38 cell lines, to name but a few examples. The dihydrofolate reductase (DHFR)-deficient mutant cell line (Urlaub et al., 1980, Proc Natl Acad Sci USA 77:4216-4220), DXB11 and DG-44, are the CHO host cell lines of choice because the efficient DHFR selectable and amplifiable gene expression system allows high level recombinant polypeptide expression in these cells (Kaufman R. J., 1990, Meth Enzymol 185:527-566). In addition, these cells are easy to manipulate as adherent or suspension cultures and exhibit relatively good genetic stability. In addition, new animal cell lines can be established using methods well known by those skilled in the art (e.g., by transformation, viral infection, and/or selection, etc.).

By in vitro cell culture is meant the growth and propagation of cells outside of a multicellular organism or tissue. Typically, in vitro cell culture is performed under sterile, controlled temperature and atmospheric conditions in containers such as tissue culture plates (e.g., 10 cm plates, 96 well plates, etc.), or other adherent culture (e.g., on microcarrier beads) or in suspension culture such as in roller bottles. Cultures can be grown in containers such as shake flasks, small scale bioreactors, and/or large-scale bioreactors. A bioreactor is a device used to culture animal cells in which environmental conditions such as temperature, atmosphere, agitation, osmolality and/or pH can be monitored and adjusted. A number of companies (e.g., ABS Inc., Wilmington, Del.; Cell Trends, Inc., Middletown, Md.) as well as university and/or government-sponsored organizations (e.g., The Cell Culture Center, Minneapolis, Minn.) offer cell culture services on a contract basis.

Further, the recombinant, mammalian cell cultures of the invention (adherent or non-adherent and growing or growth arrested), can be small scale cultures, such as for example in 100 ml containers having about 30 ml of media, 250 ml containers having about 80 to about 90 ml of media, 250 ml containers having about 150 to about 200 ml of media. Alternatively, the cultures can be large scale such as for example 1000 ml containers having about 300 to about 1000 ml of media, 3000 ml containers having about 500 ml to about 3000 ml of media, 8000 ml containers having about 2000 ml to about 8000 ml of media, and 15000 ml containers having about 4000 ml to about 15000 ml of media.

Optimal periods for which the cultures are in contact with betaine are for longer than the typical period for one normal growth cycle (e.g., for Chinese hamster ovary cells (CHO cells), where one growth cycle has been reported to be approximately 20-22 hours (Rasmussen et al., (1998) Cytotechnology, 28:31-42)). As such, in a preferred embodiment, the cultures comprise betaine preferably for at least about 20 hours, more preferably for about 22 hours, more preferably for about one day, more preferably for about 2 days, more preferably for about 3 days, more preferably for about 4 days, more preferably for about 5 days and even more preferably for about 7 days.

Additionally, the methods of the invention can be applied to perfused cell cultures. Perfused cell cultures are typically cultured continuously and can be grown for as little as about five days and for long as about nine months or longer, but are typically cultured for about 25 days. Thus, it is contemplated that betaine can be included in perfused culture media either continuously, or intermittently over the course of the perfused culture run.

For the purposes of the invention, the cells may be growing or induced to stop growing, e.g., senescent, by a method or reagent commonly used in the art, such as for example radiation or drugs. Alternatively, the cells may become growth arrested by virtue of overgrowth and crowding in the container. Thus, the culture medium can comprise betaine during either growth or senescence of the cells, including during passaging of cells, amplification of cells, growth of cells during recombinant polypeptide production stages, feeding of cell cultures during any of the foregoing, and/or during freezing and storage of cells. Further, in feeding of growing cultures, betaine can be added in variable concentrations to pulse the culture with high concentrations, followed by a removal of the betaine. For example, the cells can be grown during a proliferative phase in the absence of betaine, and then in an induction phase in the presence of betaine. Alternatively, betaine can be present during both proliferative and induction phases.

Further, the methods of the invention can be used in combination with known or yet to be discovered methods of inducing the production of recombinant proteins. By "inducing conditions" is meant a technique to increase the relative production per cell of a desired recombinant protein. Such techniques include cold temperature shift, and additions of chemicals such as alkanoic acid (including butyrate compounds, as described in U.S. Pat. No. 5,705,364 to Etcheverry et al., incorporated herein by reference), DMSO, DMF, DMA, TNF-alpha, phorbol 12-myristate 13-acetate, PMA, propionate, forskolin, dibutyryl cAMP, 2-aminopurine, adenine, adenosine, okadaic acid, and combinations of any of these techniques, to name just a few examples, as well as any yet to be described and/or discovered induction techniques. Typically, a batch culture of cells at high density is induced to produce the recombinant protein. Often, other cell processes (such as growth and division) are inhibited so as to direct most of the cells energy into recombinant protein production.

The invention finds particular use because it increases production of secreted recombinant polypeptides, in part because the cell cultures have increased numbers of viable cells. In addition, in some embodiments, the methods and compositions of the invention result in an increase of the desired folding of the secreted recombinant polypeptide. And in additional embodiments, the methods and compositions of the invention result in an increase in the amount of secreted recombinant polypeptide that is active in the desired activity, for example, recombinantly expressed TNFR-Fc that binds with high affinity to tumor necrosis factor.

Tissue culture medium is defined, for purposes of the invention, as a medium suitable for growth of animal cells, and preferably mammalian cells, in in vitro cell culture. Typically, tissue culture medium contains a buffer, salts, energy source, amino acids, vitamins and trace essential elements. In addition, the medium can oftentimes require additional components such as growth factors, lipids, and/or other serum components (e.g., transferrin).

Any medium capable of supporting growth of animal cells in culture can be used; the invention is broadly applicable to animal cells in culture, particularly mammalian cells, and the choice of medium is not crucial to the invention. Tissue culture media suitable for use in the invention are commercially available from ATCC (Manassas, Va.). For example, any one or combination of the following media can be used: RPMI-1640 Medium, Dulbecco's Modified Eagle's Medium, Minimum Essential Medium Eagle, F-12K Medium, Iscove's Modified Dulbecco's Medium. Often, depending upon the requirements of the particular cell line used, medium also contains a serum additive such as Fetal Bovine Serum, or a serum replacement. Examples of serum-replacements (for serum-free growth of cells) are TCH™, TM-235™, and TCH™; these products are available commercially from Celox (St. Paul, Minn.). When defined medium that is serum-free and/or peptone-free is used, the medium is usually highly enriched for amino acids and trace elements (see, for example, U.S. Pat. No. 5,122,469 to Mather et al., and U.S. Pat. No. 5,633,162 to Keen et al.).

Serum adds to the expense of cell culture, and problems arise from variance between serum lots and serum quality, in addition, there are serious regulatory concerns about viral contamination in serum and further, removing serum proteins from downstream processing is burdensome, as such, in a preferred embodiment the medium is serum free or essentially free of serum and the recombinant polypeptide producing cell lines have been selected for growth without serum (Rasmussen et al., (1998) Cytotechnology 28:31-42). Essentially serum free media is meant to include very low amounts of serum in the culture media. This includes less than about 2% serum, more preferably less than about 1% serum, more preferably less than about 0.5% serum, and even more preferably less than about 0.25% serum. In another preferred embodiment, the recombinant cell line is a dihydrofolate reductase negative, CHO cell line, adapted for growth without serum.

Added to the medium is an effective amount of betaine. An effective amount of betaine is that amount that is capable of increasing cell survival of a culture wherein osmotic conditions are approximately physiological, i.e., 292 mOsm. In further embodiments, the osmolality is within 100 mOsm of physiological, more preferably within 75 mOsm of physiological, still more preferably within 50 mOsm of physiological, yet more preferably within 40 mOsm of physiological, even more preferably within 30 mOsm of physiological, still even more preferably within 20 mOsm of physiological and most preferably within 10 mOsm of physiological osmolality. An improvement in cell survival is measured as an increase in cells in a betaine treated culture relative to the number of cells in untreated cultures, wherein cell survival is increased 5%, more preferably cell survival is increased 10%, more preferably cell survival is increased 15%, more preferably cell survival is increased 20%, more preferably cell survival is increased 25%, more preferably cell survival is increased 30%, more preferably cell survival is increased 35%, more preferably cell survival is increased 40%, more preferably cell survival is increased 45%, and even more preferably cell survival is increased 50%.

Betaine can be produced in different forms including as a glycine betaine. Other preferred betaines include but are not limited to betaine aldehyde and all betaine derivatives therefrom and therein.

The concentration of such compounds to use in the invention can be determined by those skilled in the art by, for example, comparing the cell death inhibitory activity of glycine betaine against that of another isoform of betaine, and extrapolating appropriate concentrations therefrom. The extrapolated concentrations can then be used as a starting point to determine the range of effective amounts of compound that should be added to a culture medium, which amounts can then be determined using small scale experiments such as those described herein. In preferred embodiments, the betaine is glycine betaine and is in the culture medium at about 10 to 60 mM 100 mM betaine, more preferably 5 to 75 mM betaine, more preferably about 10 to 60 mM betaine, and more preferably about 20 to 40 mM betaine.

The invention finds particular utility in improving the production of recombinant polypeptides via cell culture processes. The cell lines used in the invention can be genetically engineered to express a polypeptide of commercial or scientific interest. By genetically engineered is meant that the cell line has been transfected, transformed or transduced with a recombinant polynucleotide molecule, and/or otherwise altered (e.g., by homologous recombination and gene activation or fusion of a recombinant cell with a non-recombinant cell) so as to cause the cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989).

Particularly preferred polypeptides for expression are polypeptide-based drugs, also known as biologics. Preferably, the polypeptides are expressed as extracellular products, which can be either secreted into the culture medium or transmembrane, i.e., having a portion of the polypeptide extruding through the cell membrane into the extracellular milieu. Recombinant polypeptides that can be produced using the invention include but are not limited to Flt3 ligand, CD40 ligand, erythropoietin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, nerve growth factors, glucagon, interleukins 1 through 18, colony stimulating factors, lymphotoxin-$\beta$, tumor necrosis factor, leukemia inhibitory factor, oncostatin-M, and various ligands for cell surface molecules Elk and Hek (such as the ligands for eph-related kinases, or LERKS). Descriptions of polypeptides that can be produced according to the invention may be found in, for example, *Human Cytokines: Handbook for Basic and Clinical Research, Vol. II* (Aggarwal and Gutterman, Eds. Blackwell Sciences, Cambridge Mass., 1998); *Growth Factors: A Practical Approach* (McKay and Leigh, Eds. Oxford University Press Inc., New York, 1993) and *The Cytokine Handbook* (A W Thompson, ed.; Academic Press, San Diego Calif.; 1991).

Production of the receptors for any of the aforementioned polypeptides can also be improved using the invention, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such polypeptides are described in U.S. Pat. No. 5,767,064, incorporated herein by reference in its entirety.

Other polypeptides that can be produced using the invention include cluster of differentiation antigens (referred to as CD polypeptides), for example, those disclosed in *Leukocyte Typing VI* (*Proceedings of the VIth International Workshop and Conference*; Kishimoto, Kikutani et al., Eds. Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the tumor necrosis factor (TNF) receptor family, which also includes 41BB and OX40; the ligands are often members of the TNF family (as are 41 BB ligand and OX40 ligand); accordingly, members of the TNF and TNF receptor (TNFR) families can also be produced using the present invention.

Polypeptides that are enzymatically active can also be produced according to the instant invention. Examples include metalloproteinase-disintegrin family members, various kinases, glucocerebrosidase, alpha-galactosidase A, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active polypeptides can also be produced by applying the instant invention.

The inventive compositions and methods are also useful for production of other types of recombinant polypeptides, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant polypeptides such as single chain antibodies, antibodies with enhanced affinity, or other antibody-based polypeptides (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397). Recombinant cells producing fully human antibodies (such as are prepared using transgenic animals, and optionally further modified in vitro), as well as humanized antibodies can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. For example, the invention can be used to induce the expression of human and/or humanized antibodies that immunospecifically recognize specific cellular targets, e.g., any of the aforementioned polypeptides, the human EGF receptor, the her-2/neu antigen, the CEA antigen, Prostate Specific Membrane Antigen (PSMA), CD5, CD11a, CD18, NGF, CD20, CD45, Ep-cam, other cancer cell surface molecules, TNF-alpha, TGF-b1, VEGF, other cytokines, alpha 4 beta 7 integrin, IgEs, viral polypeptides (for example, cytomegalovirus) etc., to name just a few.

Various fusion polypeptides can also be produced using the invention. A fusion polypeptide is a polypeptide, or domain or a polypeptide (e.g. a soluble extracellular domain) fused to a heterologous polypeptide or peptide. Examples of such fusion polypeptides include polypeptides expressed as a fusion with a portion of an immunoglobulin molecule, polypeptides expressed as fusion polypeptides with a zipper moiety, and novel polyfunctional polypeptides such as a fusion polypeptides of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion polypeptide and a zipper fusion polypeptide, respectively; the techniques discussed therein are applicable to other polypeptides. Another fusion polypeptide is a recombinant TNFR:Fc, also known as "entanercept." Entanercept is a dimer of two molecules of the extracellular portion of the p75 TNF alpha receptor, each molecule consisting of a 235 amino acid TNFR-derived polypeptide that is fused to a 232 amino acid Fc portion of human IgG1. In fact, any of the previously described molecules can be expressed as a fusion polypeptide including but not limited to the extracellular domain of a cellular receptor molecule, an enzyme, a hormone, a cytokine, a portion of an immunoglobulin molecule, a zipper domain, and an epitope.

The resulting expressed polypeptide can then be collected. In addition the polypeptide can purified, or partially purified, from such culture or component (e.g., from culture medium or cell extracts or bodily fluid) using known processes. By "partially purified" means that some fractionation procedure, or procedures, have been carried out, but that more polypeptide species (at least 10%) than the desired polypeptide is present. By "purified" is meant that the polypeptide is essentially homogeneous, i.e., less than 1% contaminating polypeptides are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

The invention also optionally encompasses further formulating the polypeptides. By the term "formulating" is meant that the polypeptides can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the polypeptide, in combination with other components such as a physiologically acceptable diluent, carrier, or excipient. The term "physiologically acceptable" means a non-toxic material that does not interfere with the effectiveness of the biological activity of the active ingredient(s).

The invention having been described, the following examples are offered by way of illustration and not limitation.

EXAMPLE

Betaine in Culture Medium

TNFR-Fc production in some CHO cell lines results in greater quantities of recombinant protein product but with lower viability than other cell lines during the final days of the run. The decreased viability correlates with increased protease activity in the culture supernatant, a result of dying cells releasing proteases into the media, which decreases stability of the final purified product. The current study was performed to determine if betaine could prolong viability at production osmolality (250-280 mOsm initial value).

The bioreactors used for this study were stirred vessels with a 1 liter working volume, with temperature, pH and $dO_2$ control. The medium was serum-free with bicarbonate, IGF-1 (LongR3; GroPep, Australia), intralipids and peptones added. Betaine was added to 1 L bioreactor cultures of TNFR-Fc producing cells at 0, 10, 20, 30, and 40 mM with the osmolality of each culture adjusted to 270 to 280 mOsm with an appropriate amount of NaCl. The reactors were induced to express recombinant protein on day 2 by reducing the temperature and adding butyrate to 0.5 mM. Daily samples were taken for analysis of metabolic and productivity parameters.

Based on the viable cell density (VCD) profiles, betaine has a positive effect on cell viability, which is most noticeable after day 5 (FIG. 1). There was a titration effect up to 30 mM, after which higher concentrations did not increase viability as much. The ability of induced cells to produce TNFR:Fc was not decreased in the presence of betaine. Furthermore, in the presence of betaine, the percentage of the secreted recombinant polypeptide having the desired conformation increased by 17.7%, i.e., native conformation and dimerized, as measured by running the samples through hydrophobic interaction chromatography (HIC) and comparing to known controls.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawing. Such modifications are intended to fall within the scope of the appended claims.

What is claimed is:

1. A method comprising culturing a recombinantly engineered cell line in culture medium in normal osmotic conditions, wherein the cell line is recombinantly engineered to express a polypeptide of interest, the medium has an effective amount of betaine, whereby cell survival and expression of said polypeptide of interest are improved relative to cells grown without betaine, wherein the cells are grown during a proliferative phase in the absence of betaine, and in the presence of betaine in an induction phase.

2. The method of claim 1 wherein the cell line is a non-animal cell line.

3. The method of claim 1 wherein the cell line is a prokaryotic cell line.

4. The method of claim 3 wherein the prokaryotic cell line is an *E. coli* cell line.

5. The method of claim 2 wherein the cell line is an insect cell line.

6. The method of claim 5 wherein the insect cell line is an Sf9 cell line.

7. The method of claim 2 wherein the cell line is a plant cell line.

8. The method of claim 2 wherein the cell line is a yeast cell line.

9. The method of claim 1, wherein the betaine is selected from the group consisting of glycine betaine and betaine aldehyde.

10. The method of claim 9, wherein the betaine is at a concentration of about 20 mM.

11. The method of claim 10, wherein the polypeptide of interest is selected from the group consisting of a soluble TNF receptor, a soluble IL-4 receptor, a soluble IL-1 type II receptor, a soluble flt3 ligand, a soluble CD40 ligand, an erythropoietin, an antibody, an Fc-fusion protein, a calcitonin, a growth hormone, an insulin, an insulinotropin, insulin-like growth factors, a parathyroid hormone, an interferons, a nerve growth factor, a glucagons, an interleukins, a colony stimulating factor, a glucocerebrosidase, a superoxide dismutase, a tissue plasminogen activator, a Factor VIII, a Factor IX, an apolipoprotein E, an Apolipoprotein A-I, a globin, an IL-2 receptor, an IL-2 antagonist, alpha-1 antitrypsin, and an alpha-galactosidase A.

12. The method of claim 11, wherein the cell line is cultured in a bioreactor.

13. The method of claim 11, further comprising collecting the protein of interest.

14. The method of claim 11, wherein the cell line is grown in suspension culture.

* * * * *